(12) United States Patent
Ryu

(10) Patent No.: US 7,829,771 B2
(45) Date of Patent: Nov. 9, 2010

(54) RICE CULTIVAR C3GHI

(75) Inventor: Sunoh Ryu, Chungcheongnam-do (KR)

(73) Assignee: Korea National Open University Industry-Academic Cooperation Foundation, Seoul (KR)

( * ) Notice: Subject to any disclaimer, the term of this patent is extended or adjusted under 35 U.S.C. 154(b) by 1887 days.

(21) Appl. No.: 10/770,567

(22) Filed: Feb. 4, 2004

(65) Prior Publication Data

US 2004/0156929 A1    Aug. 12, 2004

(30) Foreign Application Priority Data

Feb. 5, 2003    (KR) .................. 10-2003-0007235

(51) Int. Cl.
*A01H 5/10*    (2006.01)

(52) U.S. Cl. .................................... 800/320.2

(58) Field of Classification Search ............. 800/260, 800/320.2

See application file for complete search history.

(56) References Cited

PUBLICATIONS

Gutek et al. 1981. Crop Sci 21: 79-82.*
Reddy et al. 1995. Theor Appl Genet 91: 301-312.*

* cited by examiner

*Primary Examiner*—David H Kruse
*Assistant Examiner*—Keith O. Robinson
(74) *Attorney, Agent, or Firm*—Birch, Stewart, Kolasch & Birch, LLP.

(57) ABSTRACT

A novel rice cultivar, designated C3GHi, is disclosed. The invention relates to the seeds of rice cultivar C3GHi, to the plants of rice C3Ghi, which contain 2371 mg of cyanidin 3-glucoside pigment per 100 g of seeds, of which pigment content is much higher than an existing rice cultivar Heugjinju.

3 Claims, 6 Drawing Sheets

RICE CULTIVAR C3GHI

FIELD OF THE INVENTION

This Non-provisional application claims priority under 35 U.S.C. §119(a) on Patent Application No(s). 10-2003-0007235 filed in Korea on Feb. 5, 2003, the entire contents of which are hereby incorporated by reference.

The present invention relates to a novel rice cultivar, designated C3 GHi (ACCESSION NO. KCTC 11616BP). The invention further relates to a novel rice cultivar, designated C3 GHi, which contains high levels of cyanidin 3-glucoside, a natural antioxidant. The invention also provides a method for breeding seeds of rice cultivar C3GHi.

BACKGROUND OF THE INVENTION

Generally, the color of food changes as storage time goes by. The color of food, that is, natural pigment changes according to storage condition or degree of processing, and the change of color is followed by quality deterioration.

Meanwhile, edible pigment is generally used to cooking process of food.

It is advisable to use natural edible pigment but natural pigment is difficult to separate and purify, and the price is mostly high.

Therefore, artificial pigment is generally used to cooking process of food, but harmfulness of artificial pigment to human body is under discussion and it is related to the problem of safety. So detection, separation and purification of natural pigment are important.

Anthocyanin from grape skin is mostly known as natural pigment and 100 g of grape contains about 450~1,600 mg of anthocyanin.

Anthocyanin pigment has been used for addition agent of confectionery, gum, rice cake or alcoholic liquors and its antioxidant or thrombolytic activity has been known. Meanwhile, cyanidin 3-glucoside from rice cultivar Heugjinju is natural pigment which belongs to anthocyanin group.

This pigment is more stable than the anthocyanin pigment against the change of light, temperature or pH and its extraction method has been disclosed by Korea patent (KR 294731).

The cyanidin 3-glucoside is called "Kuromanin", which belongs to anthocyanin group.

According to studies, this pigment is superior to free-radical elimination and especially its absorbability of active oxygen which is harmful to human body is so excellent that it can be used for antioxidant system.

It is the purple to black-purple pigment distributed over seed coat and peel of rice. The content of the pigment depends on rice cultivar or percentage of rice kernel. For example, rice cultivar Suwon425 contains 163 mg of cyanidin 3-glucoside per 100 g of seeds, rice cultivar Heugjinju contains 552 mg.

7% of rice kernel contains 15,480 mg of cyanidin 3-glucoside per 100 g of seeds, 14% of rice kernel contains 12,930 mg and 21% of rice kernel contains 6,325 mg. Although there is difference of the pigment content depending on rice cultivar or rice kernel, the present invention provides novel rice cultivar of which pigment content is 4 times as much as the existing rice cultivar Heugjinju.

SUMMARY OF THE INVENTION

According to the invention, there is provided a novel rice cultivar, designated C3GHi. This invention thus relates to the seeds of rice cultivar C3GHi (Accession No. KCTC 11616BP), to the plants of rice C3GHi.

Thus, any such methods using the rice variety C3GHi are part of this invention: selfing, backcrosses, hybrid production, crosses to populations, and the like. All plants produced using rice variety C3GHi as a parent are within the scope of this invention. Advantageously, the rice variety could be used in crosses with other, different, rice plants to produce first generation ($F_1$) rice hybrid seeds and plants with superior characteristics.

In another aspect, the present invention provides for use of rice cultivar C3GHi for antioxidants and thrombolytic agents.

DEFINITIONS

In the description and tables which follow, several terms are used. In order to provide a clear and consistent understanding of the specification and claims, including the scope to be given such terms, the following definitions are provided:

C3G. C3G means cyanidin 3-glucoside.

C3GHi. C3GHi is name of the novel rice cultivar and it means C3G high.

DESCRIPTION OF THE PREFERRED EMBODIMENTS

First Embodiment

Breeding of Novel Rice Cultivar, C3GHi

Figures 1, 2:
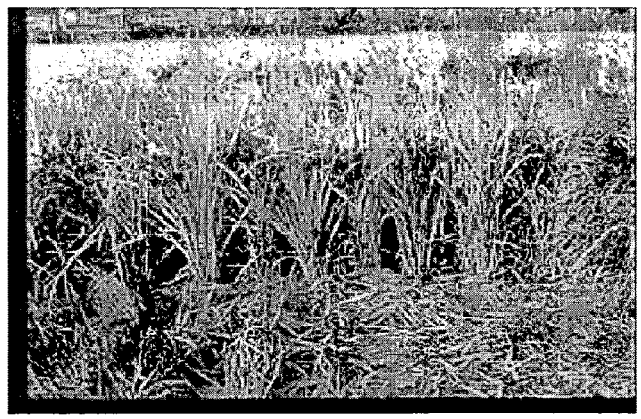
FIG. 1 illustrates flow chart of breeding C3GHi to the 9th generation.
FIG. 2 illustrates field test result of novel rice cultivar C3GHi.
Figure 3A:
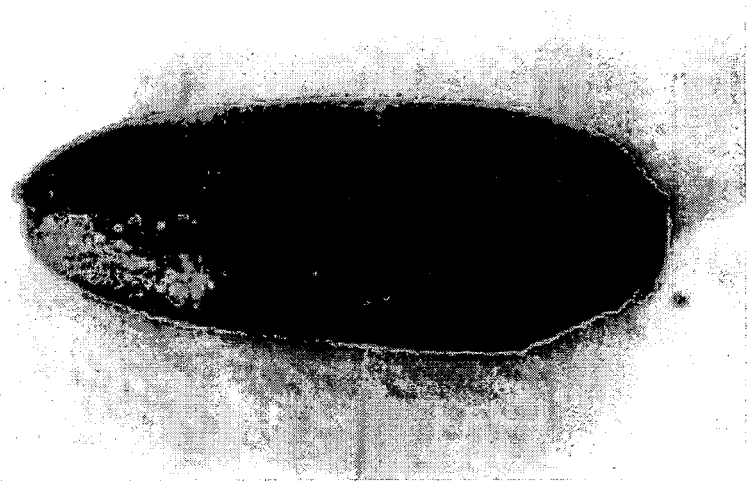
FIG. 3(a) illustrates photo showing seeds of rice cultivar C3GHi.
Figure 3B:
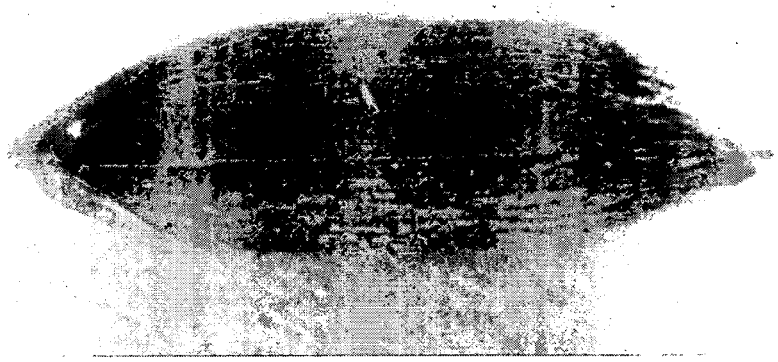
FIG. 3(b) illustrates photo showing seeds of general rice cultivar.
Figure 4A:
FIG. 4(a) illustrates photo showing collection of seeds of rice cultivar C3GHi.
Figure 4B:
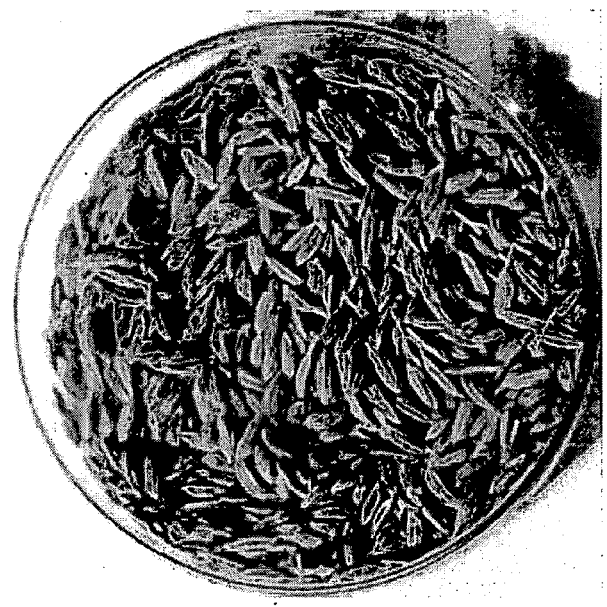
FIG. 4(b) illustrates photo showing collection of seeds of rice cultivar Heugjinju.

As shown in FIG. 1, novel rice cultivar C3GHi (seeds deposited Jan. 5, 2010, with the Korean Collection for Type Cultures (KCTC), Biological Resource Center (BRC), Korea Research Institute of Bioscience and Biotechnology (KRIBB), 111 Gwahangno, Yuseong-gu, Daejeon 305-806, Korea, under the Accession Number KCTC 11616BP) of the present invention is produced by crossing rice cultivar Suwon425 (purchased from National Institute Crop Science under Rural Development Administration of Korea, which is located in 151, Seodun-dong, Gwonseon-gu, Suwon, Gyeonggi-do, Republic of Korea) as paternity with rice cultivar Heugjinju as maternity and selfing $F_1$.

Two parents which possess favorable, complementary traits are crossed to produce an $F_1$. $F_2$ population is produced by selfing said $F_1$ hybrid. Selection of the best individuals may begin in the $F_2$ population. Selfing and selection is repeated for obtaining $F_9$.

The result of selfing is that $F_1$ contains 355 mg of cyanidin 3-glucoside per 100 g of seeds, $F_2$ contains 620 mg, $F_1$ contains 1322 mg . . . etc. And $F_9$ contains 2371 mg of cyanidin 3-glucoside per 100 g of seeds.

The result of field progeny test has confirmed characteristics of novel rice cultivar, which found to be uniform and stable.

After the last selfing and selection, the stable rice cultivar is named "C3GHi".

Second Embodiment

Evaluation of Cyanidin 3-Glucoside Content

Figure 5:
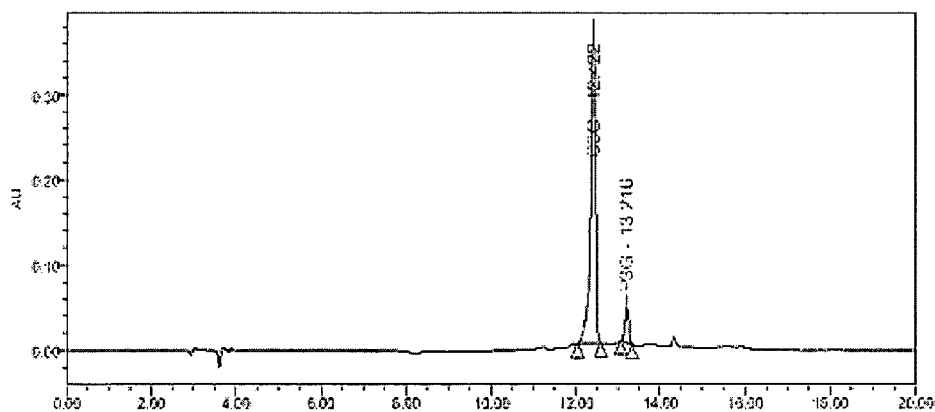
FIG. 5 illustrates chromatogram of cyanidin 3-glucoside from the rice cultivar C3GHi.
Figure 6:
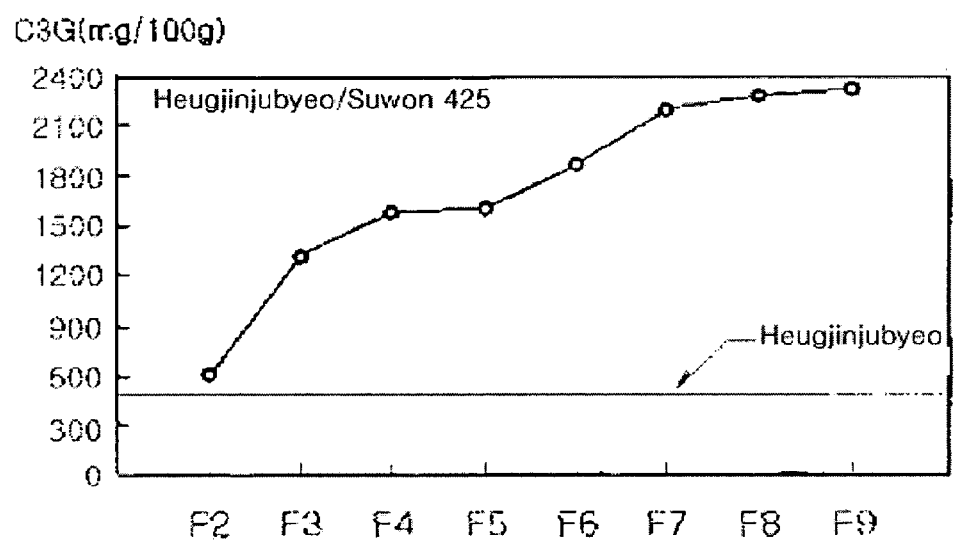
FIG. 6 illustrates cyanidin 3-glucoside content of hybrid generation of the rice cultivar C3GHi.

Table 1 and FIG. 5 shows analysis of cyanidin 3-glucoside contents of the C3GHi and other rice cultivar. Samples of each rice cultivar were pulverized and extracted several times with 95% (v/v) of ethanol containing 0.5% (v/v) of TFA.

The extract was concentrated and passed through a sep-pac column and then carried out quantitative analysis by HPLC.

The condition for HPLC analysis was as follows;
Column phase: Develosil ODS-5
Column size: 4.6×250 mm
Eluent: gradient 0.1% (v/v) TFA in water to 0.1% (v/v) TFA in methyl cyanide (30 min)
Flow rate: 1.0 ML/min
Temperature: RT
Detection: 530 nm (12.442 min)

Table 1 shows analysis of cyanidin 3-glucoside contents of the C3GHi and other rice cultivar.

| Rice Cultivar | C3G content per 100 g of seeds (mg) |
|---|---|
| Heugjinju | 552 |
| Sanghaehyanghyeolla | 163 |
| Heugnam | 191 |
| Hong Shei Lo | 221 |
| Cheng Chang | 321 |
| Mitax | 186 |
| PI 60979-1 | 186 |
| C3GHi (Accession No. KCTC 11616BP) | 2371 |

Third Embodiment

Assay of Antioxidant Activity

Antioxidant activities of C3GHi and other rice cultivar were assayed.

Figure 7A:
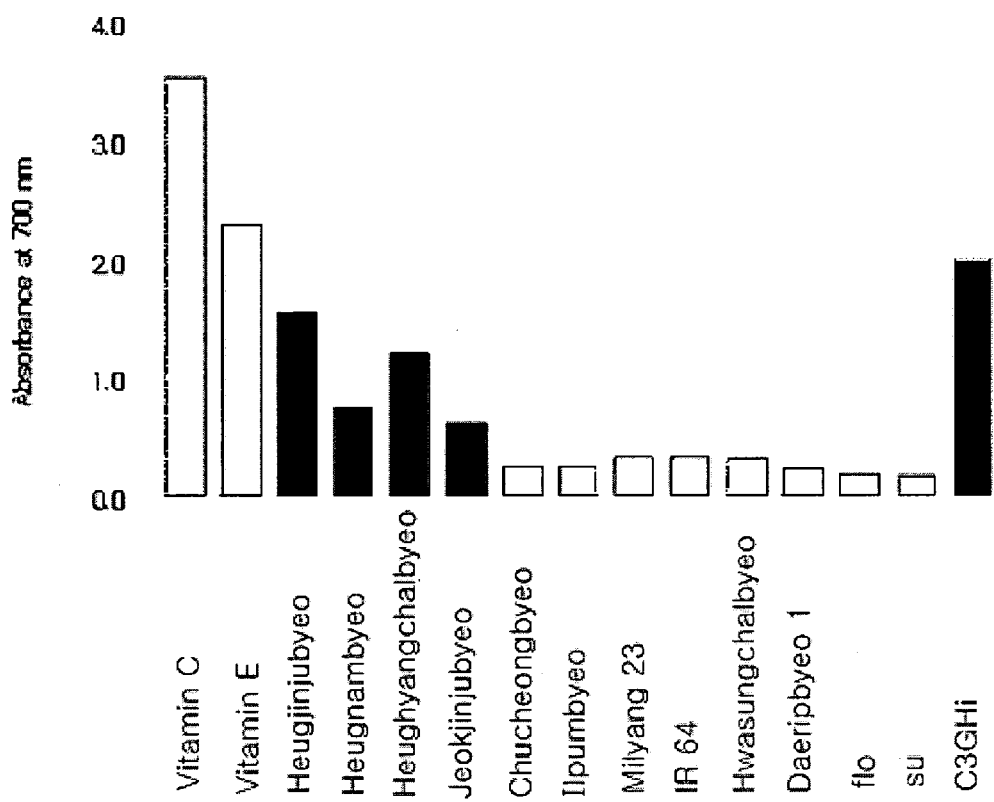
FIG. 7(a) illustrates antioxidant activity and free-radical scavenging activity of the rice cultivar C3GHi.
Figure 7B:
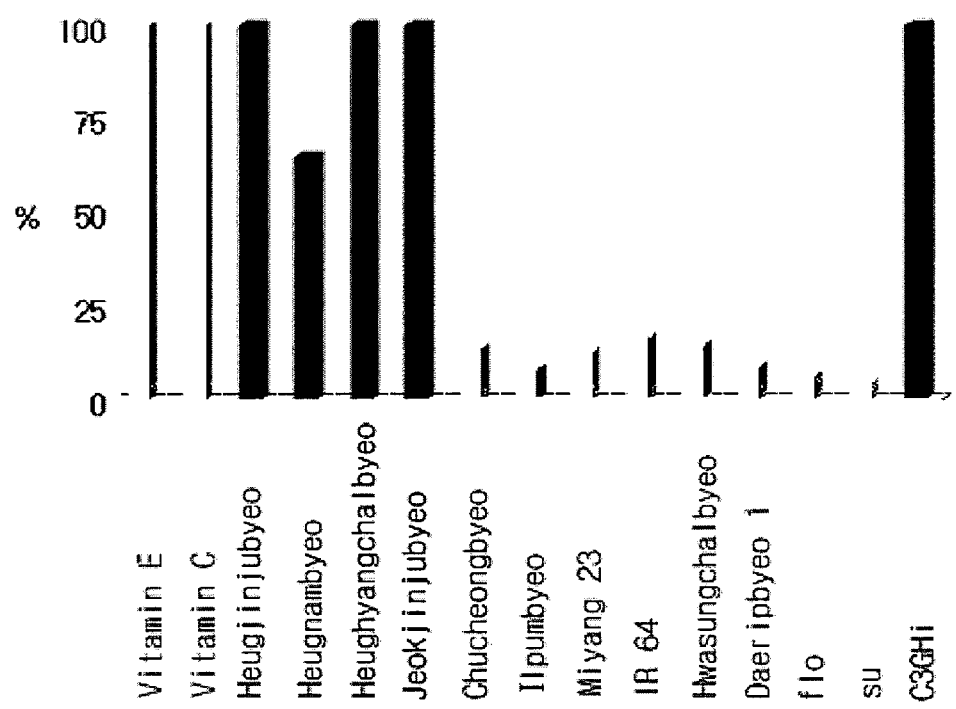
FIG. 7(b) illustrates antioxidant activity and free-radical scavenging activity of the existing rice cultivar.

C3GHi and other rice cultivar were extracted with 80% of MeOH and quantitative analysis of the extract was carried out by measuring reducing power (measuring OD at 700 nm). FIG. 7(*a*) shows the result.

Meanwhile, 10 ppm of the extract of C3GHi was evaluated for free-radical scavenging activity using DPPH method and the result was that free-radical scavenging activity of C3GHi is equal to the activity of vitamin E or vitamin C.

Fourth Embodiment

Assay of Thrombolytic Activity

Thrombolytic activities of C3GHi and other rice cultivar were assayed.

The condition for analysis was as follows;
Sample: rice cultivar Dongjin, C3GHi
Extractant: EtOH
Coagulation inducing factors: Adenosine Diphospate, Collagen, Arachidonic acid
Concentration of fraction: 2.5 mg/ML

TABLE 2

| Blood platelet coagulation factor | Concentration of extract (mg/ML) | | | |
|---|---|---|---|---|
| | C3GHi | | Dongjin | |
| | 2 | 5 | 2 | 5 |
| Adenosine Diphospate | ± | ± | ++ | + |
| Collagen | ± | ± | ++ | + |
| Arachidonic Acid | ± | ± | + | + |

−: very strong,
±: strong,
+: middle,
++: weak,
+++: very weak

What is claimed is:

1. A rice seed designated C3GHi with the Accession Number KCTC 11616BP, containing 2371 mg of cyanidin 3-glucoside per 100 g of seed, a natural antioxidant pigment which belongs to anthocyanin group.

2. A composition for antioxidant activity or thrombolytic activity comprising the seed of claim 1.

3. The composition according to claim 2, characterized in that said composition is a food composition or pharmaceutical composition.

* * * * *